United States Patent [19]

Sherman

[11] 4,223,681
[45] Sep. 23, 1980

[54] VALIDATION OF BLOOD PRESSURE

[75] Inventor: Allan P. Sherman, Lexington, Mass.

[73] Assignee: Hewlett-Packard Company, Palo Alto, Calif.

[21] Appl. No.: 894,873

[22] Filed: Apr. 10, 1978

[51] Int. Cl.² ............................................. A61B 5/02
[52] U.S. Cl. .................................. 128/672; 364/417; 364/575
[58] Field of Search .................... 128/2.05 A, 2.05 M, 128/2.05 Q, 2.05 R, 672, 682, 687, 702–706; 364/575, 734, 811, 415–417; 328/115–117; 307/358

[56] References Cited

U.S. PATENT DOCUMENTS 3,648,688  3/1972  O'Hanlon, Jr. ..................... 364/486

Primary Examiner—William E. Kamm
Assistant Examiner—Francis J. Jaworski
Attorney, Agent, or Firm—Donald N. Timbie

[57] ABSTRACT

Signals having desired peaks and undesired peaks that may be due to noise are processed so as to identify the desired peaks by determining a first difference between the amplitude of every peak and a long-term average of the peak amplitudes and then obtaining a second difference between the first difference and the average of such first differences. If the second difference exceeds a predetermined amount, the peak is considered to be undesired; but if the second difference is less than the predetermined amount, the peak is considered to be desired. If the desirable peaks represent systolic or diastolic blood pressures, their respective averages are considered to be unreliable if the number of desired peaks occurring within a given time is less than an arbitrarily selected number; and if the ratio of undesirable to desirable peaks is less than a predetermined amount, the signal is considered to be of poor quality so that the averages attained are suspect.

19 Claims, 9 Drawing Figures

VALIDATION OF BLOOD PRESSURE

BACKGROUND OF THE INVENTION

In monitoring the physiological condition of a patient, it is often desirable to display the variations in systolic, mean and diastolic blood pressures that have occurred over a number of hours. Systolic pressures are produced when the heart contracts so as to produce maximum pressure peaks in the blood pressure signal, and diastolic pressures are produced when the heart relaxes so as to produce minimum pressure peaks in the blood pressure signal. Ideally, there would be one maximum peak and one minimum peak for each heart cycle, so that the respective averages of the amplitudes of the maximum and minimum peaks occurring during a time period, such as a minute, could be plotted to form what is known as a "trend plot". In practice, however, the blood pressure signal contains peaks due to noise that have no physiological significance, so that their inclusion in the averages is a source of error. The effect of noise peaks can be reduced by signal processing means such as set forth in my copending U.S. Pat. application Ser. No. 894,679 filed concurrently herewith and entitled Derivation of Steady Values of Blood Pressures, and reasonably steady values of the peak blood pressures produced, but the values can be affected by continued bursts of noise. Furthermore, certain medical procedures cause interruptions in the blood pressure signal that make the average pressures derived from it unreliable.

BRIEF DISCUSSION OF THE INVENTION

In accordance with this invention therefore, whether or not the signal processing means of the aforesaid patent application is used, the signals representing the maximum and minimum peaks of the blood pressure signal are processed in such manner as to tend to eliminate those that are due to noise and retain those that represent true systolic and diastolic pressures. In particular, the difference between a maximum peak and a long-term average of the maximum peaks is compared with the average of such differences. If the difference is less than a predetermined amount, the signal representing the particular peak value is considered to be valid. The signals representing minimum peaks are similarly processed to determine which ones are valid. Valid values of the mean blood pressure are derived by sampling the mean value of the blood pressure signal during each valid maximum and minimum peak. In accordance with another aspect of this invention, no peak is considered valid unless the difference between it and the mean of the blood pressure signal exceeds a given amount.

In the event that the number of valid maximum peaks or the number of valid minimum peaks occurring within an interval falls below some arbitrarily selected standard, the data is considered to be unreliable and the average for that interval may be excluded from the trend plot. In this event, a signal is produced that may be used to prevent the display of the systolic average $S_{AV}$, the diastolic average $D_{AV}$, and the mean blood pressure $M'$.

In the event that the ratio of the number of invalid peaks to the number of valid peaks is greater than a given proportion, the averages $S_{AV}$, $D_{AV}$ and the mean $M'$ are displayed, but a signal is developed that may be used to display a warning, indicating that the average peak values displayed in the trend plot may be suspect because the blood pressure signal is of poor quality.

THE DRAWINGS

FIG. 1A includes graphs of a blood pressure waveform PDATA, is approximate means BMAVG, and a waveform SMAX that represents the systolic peaks of PDATA, and a waveform SSAVG that is a long-term average of SMAX;

FIG. 1B includes a waveform SAVSC which is a longterm moving average of the differences between SMAX, or the positive peaks of the waveform PDATA, and the waveform SSAVG of FIG. 1A, and a waveform SCATR which represents the absolute value of the difference between SMAX and the moving average SSAVG;

Figure 1A:
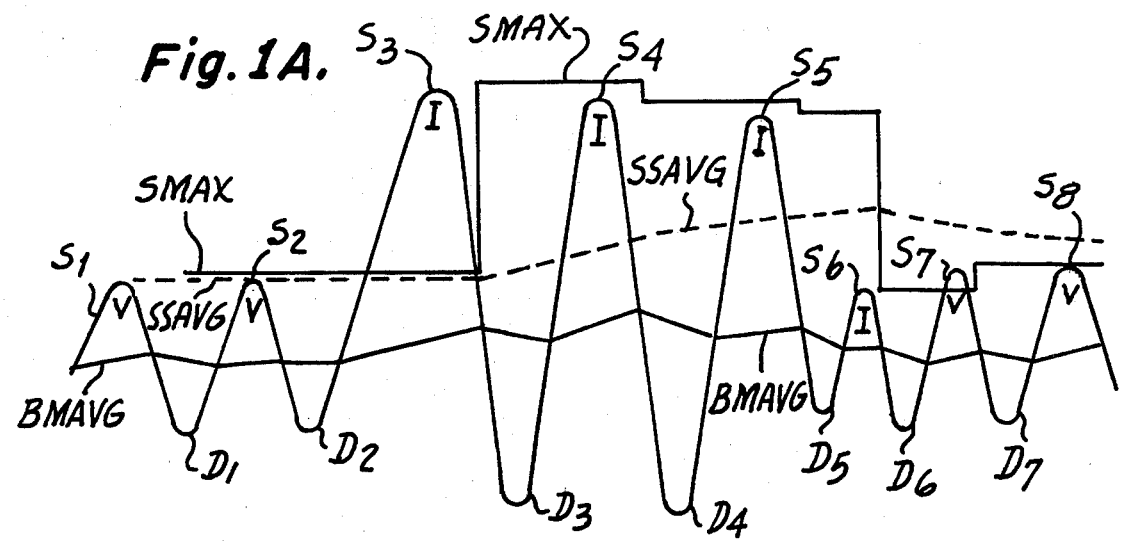
FIG. 1C illustrates certain pulses that are used in the circuit of FIG. 2 for deriving maximum and minimum values of the waveform PDATA in FIG. 1A and in identifying when new maximum or minimum values are available.
Figure 1B:
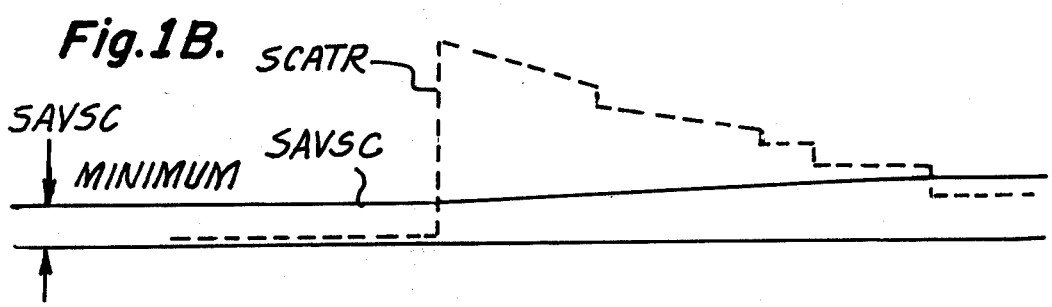
Figure 1C:
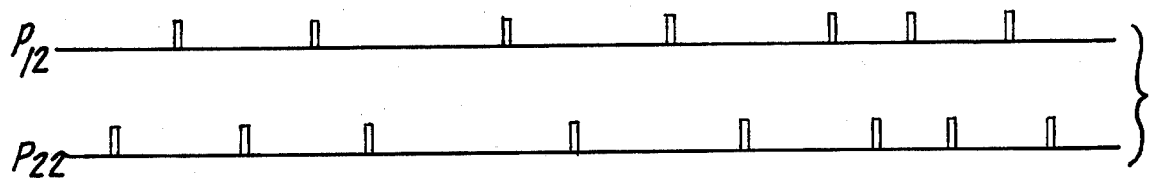

Reference is made to the graphs of FIGS. 1A through 1C for an overall illustration of the various functions involved in selecting maximum peak values to be used in the trend plot of systolic pressures in accordance with this invention. The functions for selecting the minimum peak values to be used in the trend plot of diastolic pressures are analogous but are not graphically illustrated. It is to be understood that the graphs are somewhat idealized in order to illustrate the principles involved. The wave PDATA represents variations in blood pressure; the wave BMAVG represents the approximate mean of PDATA; SMAX follows the maximum peaks $S_1$ through $S_8$; and the wave SSAVG is a long-term average of SMAX. Also included are diastolic peaks $D_1$ through $D_7$, but these are not directly involved because this invention will be explained in connection with the derivation of data for a systolic trend plot, and it will be noted that diastolic values are treated in a similar manner.

The values SMAX are measured whenever the signal PDATA drops below its mean BMAVG. The wave SCATR of FIG. 1B represents the absolute value of the difference between SMAX and the wave SSAVG, and the wave SAVSC represents a long-term moving average of the differences represented by the wave SCATR. Whenever the difference, SCATR, of a value of SMAX exceeds the moving average of such differences, SAVSC, by a predetermined amount, the value of SMAX is declared invalid and is not included in the averages used in the trend plot. Thus, in the example illustrated in FIG. 1A, the values of SMAX corresponding to the peaks $S_3$ through $S_6$ are defined to be invalid and would not contribute to the averages used in forming a trend plot.

CIRCUIT FOR OBTAINING SYSTOLIC AND DIASTOLIC VALUES

In discussing the circuit of FIG. 2, references will be made to the waveforms of FIGS. 1A through 1C where appropriate. A blood pressure signal PDATA is supplied by a source 2 to a low pass filter comprised of a resistor 4 and a capacitor 6 connected in series to ground. The filter produces a signal BMAVG at the junction 8 that is the approximate mean of PDATA. The signal BMAVG is applied to the inverting input of a comparator 10, and PDATA is applied to its noninverting input. Whenever the signal PDATA drops below its mean BMAVG, the output of the comparator 10 decreases to a low state triggering a negative edge triggered one-shoe multivibrator 12 so that it outputs one of the pulses $P_{12}$ illustrated in FIG. 1C. These pulses $P_{12}$ are applied so as to set a sample-and-hold circuit 14 at the maximum value of SMAX then at the output of a maximum peak detector 16. The pulses $P_{12}$ are then applied via a delay 17 to reset the maximum peak detector 16. A relay coil 18 that is connected between the output of the comparator 10 and a point of low state potential, $-V$, operates a switch $s_0$ that is connected to receive the signal PDATA. When the output of the comparator 10 becomes low, the switch $s_0$ is in contact with its lower terminal 18' so as to apply the signal PDATA to the input of a minimum peak detector 20. As will be subsequently explained, the pulses $P_{12}$ will be used to identify the occurrence of new data points at the terminal 28 which are to be examined for use in the trend plot.

The output of the comparator 10 is also connected to a positive edge triggered one-shot multivibrator 22, and its output is connected so as to set a sample-and-hold circuit 24, and to clear a minimum peak detector 20 via a delay 26. When the blood pressure signal PDATA crosses above its mean BMAVG, the output of the comparator 10 shifts to its high state causing the multivibrator 22 to output one of the positive pulses $P_{22}$. This sets the sample-and-hold circuit 24 at the minimum value of DMIN, appearing at the output of the minimum peak detector 20 to which it is connected. After a time determined by the delay 26, a pulse $P_{22}$ resets the minimum peak detector 20. The high state now at the output of the comparator 10 energizes the relay coil 18 so as to pull the switch $s_0$ into contact with its upper terminal 18" and apply the blood pressure signal PDATA to the input of the maximum peak detector 16. As will be subsequently explained, the pulses $P_{22}$ will be used to identify the occurrence of new data points at the terminal 28' which are to be examined for use in the trend plot.

Thus, the circuits just described that are within the dotted rectangle 27 are a means for providing a signal SMAX at a terminal 28 and a signal DMIN at a terminal 28', as well as providing pulses $P_{12}$ and $P_{22}$ which indicate when those signals are to be considered for inclusion in the trend plot.

IDENTIFICATION OF VALID SYSTOLIC VALUES

The following portion of the circuit energizes a relay coil 29 whenever the maximum value SMAX at the output of the sample-and-hold circuit 14 meets two criteria required in order for it to be considered a valid value that can be used in deriving the averages for the trend plot. The first criteria is that a value SMAX must exceed the mean BMAVG of the PDATA wave by a predetermined amount, and the second criteria is that the absolute deviation between a value SMAX and a reference signal SSAVG, which is a long-term average of the values of SMAX, must not exceed a specified long-term average of these deviations.

In order to determine whether a maximum value SMAX at the output of the sample-and-hold circuit 14 meets the first criteria, the signal SMAX at the terminal 28 and the mean signal BMAVG at the junction 8 are applied to a subtractor 30 that provides the difference, SMAX-BMAVG, to the non-inverting input of a comparator 32. Its inverting input is connected to a movable tap 34 on a potentiometer resistor 36 that is connected between a point of positive potential and ground. The output of the comparator 32 is connected to one input of an AND gate 38. Whenever the value SMAX exceeds the mean BMAVG by more than the voltage at the tap 34, the output of the comparator 32 is positive.

In order to determine whether a maximum value SMAX meets the second criteria, SMAX is coupled from the terminal 28 to one input of a subtractor 40 and to a low pass filter comprised of a resistor 41 and a capacitor 42 connected in series to ground. The resistor 41 and the capacitor 42 have values such as to form a long time constant low pass filter that provides a signal SSAVG at their junction 43. The junction 43 is connected to the other input of the subtractor 40. Whether the output, SMAX-SSAVG, of the subtractor 40 is positive or negative, a positive voltage, called SCATR that is equal to the absolute value of the difference, is provided by an absolute value circuit 44.

A voltage, SAVSC, which is the long-term average of the absolute value of the deviations, SCATR, of the maximum values of SMAX from the value of the wave SSAVG, is derived as follows. When the absolute value voltage SCATR is more positive than the voltage across a capacitor 45, the capacitor is charged through a diode 46 and a series resistor 48, and when the voltage SCATR is less positive than the voltage across the capacitor 45, the capacitor is discharged through a diode 50 and a series resistor 52. The value of the resistor 48 can be greater than the value of the resistor 52, so that the capacitor 45 is charged at a slower rate than it is discharged. An isolating non-inverting unity gain amplifier 54 and a potentiometer resistor 56 are connected in series parallel with the capacitor 45. The voltage at the movable tap 57 on the resistor 56 is the desired voltage SAVSC. It is applied through a diode 57' to the non-inverting input of a comparator 58. A minimum positive voltage for the noninverting input of the comparator 58 is established by connecting a diode 60 between the input and a movable tap 62 on a potentiometer resistor 64 that has one end connected to a point of positive potential and the other end connected to ground.

The voltage SCATR at the output of the absolute value circuit 444 is coupled to the inverting input of the comparator 58 by a potentiometer resistor 68 and its movable tap 70.

If the taps 70 and 57 are set at the ungrounded ends of their respective potentiometer resistors 68 and 56, the output of the comparator 58 is positive when the voltage SCATR at the output of the absolute value circuit 44, which represents the deviation of the current systolic value SMAX from the wave SSAVG, is less than the long-term average of such deviations, SAVSC, that is represented by the voltage across the capacitor 45. This indicates that the second criteria for a valid value has been met, so that the value of SMAX is valid. This is illustrated in FIG. 1B wherein the values of SMAX for which the voltage SCATR is less than the voltage SAVSC are valid. Variations in this criteria can be made by adjusting the taps 57 and 70.

If both criteria are met, the inputs to the AND gate 38 are both positive and the relay coil 29 is energized, signifying that the current value of SMAX is valid.

COUNTING THE VALID AND INVALID MAXIMUM VALUES

Inasmuch as the sample-and-hold circuit 14 outputs a new but not necessarily different maximum value in response to each of the pulses $P_{12}$ that are applied to it from the multivibrator 12, the number of valid maximum values that occur during any time period can be determined by counting the number of pulses $P_{12}$ that coincide with valid maximum values, and the number of invalid maximum values can be determined by counting the number of the pulses $P_{12}$ that coincide with invalid maximum values. Various methods may be used to perform this function, but in the circuit of FIG. 2, it is accomplished by coupling the pulses $P_{12}$ via a delay means 72 to a switch $s_1$. The delay is equal to the time it takes a maximum value SMAX to affect the output of the relay 29. As previously explained, when a maximum value SMAX is invalid, the relay coil 29 is not energized so that the switch $s_1$ remains in contact with a terminal I as illustrated, but when the maximum value is valid, the relay coil 29 is energized and pulls the switch $s_1$ into contact with a terminal V. The terminals I and V are respectively connected to the inputs of integrators 74 and 76 that are periodically discharged by pulses from a timer 78 via a delay 80. The time between these pulses is equal to the period such as the minute previously suggested during which averages of systolic, diastolic and mean pressure values are to be taken for data points in the trend plot display. At the end of each period, the voltages INVSY and VALSY at the outputs of the integrators 74 and 76, respectively, are proportional to the number of pulses $P_{12I}$ that are applied to the switch terminal I and the number of pulses $P_{12V}$ that are applied to the switch terminal V by the switch $s_1$.

In order to obtain a voltage indicative of the average of the valid maximum values of SMAX, the terminal 28 of the sample-and-hold circuit 14 is connected to a normally open switch $s_2$. The switch $s_2$ is placed in contact with a terminal 82 during the application of pulses $P_{12}$ from the delay means 72 to a relay coil 84. The terminal 82 is connected to one side of a normally open switch $s_3$ that is placed in contact with a terminal S' whenever the relay coil 29 is energized. The closing of the switch $s_3$, in effect, samples the maximum value SMAX at the output of the sample-and-hold circuit 14 and applies the samples of SMAX to an input of an integrator 86 that operates in response to the timing pulses from the delay means 80 in the same way as the integrators 74 and 76. One input of a divider 88 is connected to the output of the integrator 76 so as to receive its output, VALSY, and the other input is connected to the output of the integrator 86 so as to receive its output, DWASY, and provide an output voltage equal to the integrated value of the samples of valid maximum values divided by a voltage that is proportional to the number of valid maximum values that have been received. The result is a voltage, $S_{AV}$, representing the average of the valid maximum values occurring within the interval since the most recent pulse provided by the timer 78.

The average of valid minimum values, $D_{AV}$, occurring during the same time period is derived by a diastolic circuit that is the same as the circuit just described for deriving the average of the valid maximum values. It is not shown, but is contained in a rectangle 90. It requires as inputs the minimum values DMIN at the output terminal 28' of the sample-and-hold circuit 24, the pulses $P_{22}$ from the multivibrator 22, the timing pulses from the delay means 80, and the mean, BMAVG, of the PDATA signal.

DERIVATION OF THE MEAN BLOOD PRESSURE SIGNAL

Whereas the mean, BMAVG, of the blood pressure signal PDATA that is provided at the junction 8 of the resistor 4 and the capacitor 6 could be displayed as the mean of the blood pressure, its value may be affected by signals that may not accurately represent the blood pressure. Therefore, the following circuit is used to derive a mean M' that is the average of samples of the mean BMAVG taken whenever the maximum value SMAX or the minimum value DMIN is valid. Pulses $P_{12}$ from the terminal V of the switch $s_1$ that occur when the maximum values of SMAX are valid are supplied to one input of an OR device 92, and similar pulses $P_{22}$ from the diastolic circuit 90 that occur when the minimum values DMIN are valid are applied to the other input. The presence of these pulses causes the OR device 92 to output corresponding pulses to an integrator 94 that responds to timing pulses from the delay 80 in the same way as the other integrators. The integrator 94 outputs a voltage to a divider 96 that is proportional to the sum of the valid pulses $P_{12V}$ and $P_{22V}$.

The pulses at the output of the OR device 92 are also applied so as to energize a relay coil 98 and close a normally open switch $s_4$ that is connected between the input of an integrator 100 and the junction 8 where the mean BMAVG of the PDATA signal appears. The integrator 100 responds to timing pulses from the delay means 80 so as to integrate the samples M of the mean signal BMAVG thus applied to it over the same periods as the other integrators. The output DWAMN of the integrator 100 is applied to the other input of the divider 96 so as to derive a voltage M' that represents the sum of the samples M of the mean BMAVG divided by a voltage proportional to the sum of the numbers of valid pulses $P_{12V}$ and $P_{22V}$. The voltage M' at the output of the divider 96 is the average of the values of BMAVG that occur during valid pulses $P_{12V}$ and $P_{22V}$ so that M' is not affected by artifacts.

POOR SIGNAL INDICATION

If the ratio of the invalid pulses $P_{12I}$ to the valid pulses $P_{12V}$ in the systolic circuit, or if the ratio of the invalid pulses $P_{22I}$ to the valid pulses $P_{22V}$ in the diastolic circuit, is larger than a given number, the signals may be of such poor quality that a warning should be given. In the systolic circuit, a voltage equal to the ratio of the number of pulses $P_{12I}$ to the number of pulses $P_{12V}$, or INVSY to VALSY, is derived at the output of a divider 102 by connecting its inputs to the outputs of the integrators 74 and 76. This voltage is applied to the non-inverting input of a comparator 104, and a movable tap 106 on a potentiometer resistor 108 is connected to the inverting input. If the ratio of invalid pulses to valid pulses is too large, the positive voltage at the output of the divider 102 exceeds the positive voltage at the tap 106 so as to cause the output of the comparator 104 to become positive. One input of an OR device 107 is connected to the output of the comparator 104, and the other input is connected to the A output of an identical circuit contained in the rectangle 90, but not shown. If either or both inputs to the OR device 107 are positive, its output is also positive. This positive voltage can be used to give an indication that the signals are of poor quality.

INSUFFICIENT DATA

Due to certain medical procedures, the blood pressure signal PDATA may be cut off for varying periods of time. If for this or any other reason there are less than a specified number of both valid maximum and valid minimum values during a period between pulses from the timer 78, the data may be deemed insufficient for deriving reliable averages for the trend plot. In such event, it may be desirable to interrupt the display of the systolic average $S_{AV}$, the diastolic average $D_{AV}$, and the mean blood pressure M'. For this purpose, the positive voltage, VALSY, at the output of the integrator 76, which is proportional to the number of valid pulses $P_{12V}$, or what is the same thing, the number of valid maximum values SMAX, is applied to the non-inverting input of a comparator 109, and a positive voltage having a value determined by the setting of a movable tap 110 on a potentiometer resistor 112 is applied to the inverting input. The tap 110 is set at a voltage which will be produced by the integrator 76, after the selected number of valid pulses $P_{12V}$ have been applied to it. When the number of valid pulses exceeds the selected number, the output of the comparator 109 becomes positive. The output is applied to one input of an AND gate 114, and the output of a similar comparator at B in the diastolic circuit 90, but not shown, is applied to another input. The third input of the AND gate 114 is connected to the output of the timer 78. If the numbers of valid maximum pulses $P_{12V}$ represented by the voltage VALSY and the numbers of valid minimum pulses $P_{22V}$ represented by the voltage VALDI derived from the diastolic circuit 90 both exceed the minimum required for sufficient data by the time a pulse is produced by the timer 78, all the inputs of the AND gate 114 will be positive and a recorder 116 will note the values of the signals $S_{AV}$, $D_{AV}$ and M' occurring at that time, as well as any indication of a poor signal that may be provided by the OR gate 107. On the other hand, if the output of the comparator 109 in the systolic circuit or the output of the corresponding comparator, not shown, in the diastolic circuit 90, or both, are not positive when the timer 78 outputs a pulse, the output of the AND gate 114 will be negative and will prevent the recorder −16 from displaying the values of the signals $S_{AV}$, $D_{AV}$ and M'. The poor signal indication can be displayed independently so that it is not affected by the output of the AND gate 114. The details of the recorder 116 that carry out these functions are not shown because they are well understood by those skilled in the art and because the detailed manner in which the trend data is displayed is not part of this invention. The purpose of the delay means 80 is to permit time following a pulse from AND gate 114 for the voltages at the outputs of the various integrators to be used by the circuits coupled to them before the outputs are erased by application of the delayed timing pulses.

COMMENT

Figure 2:
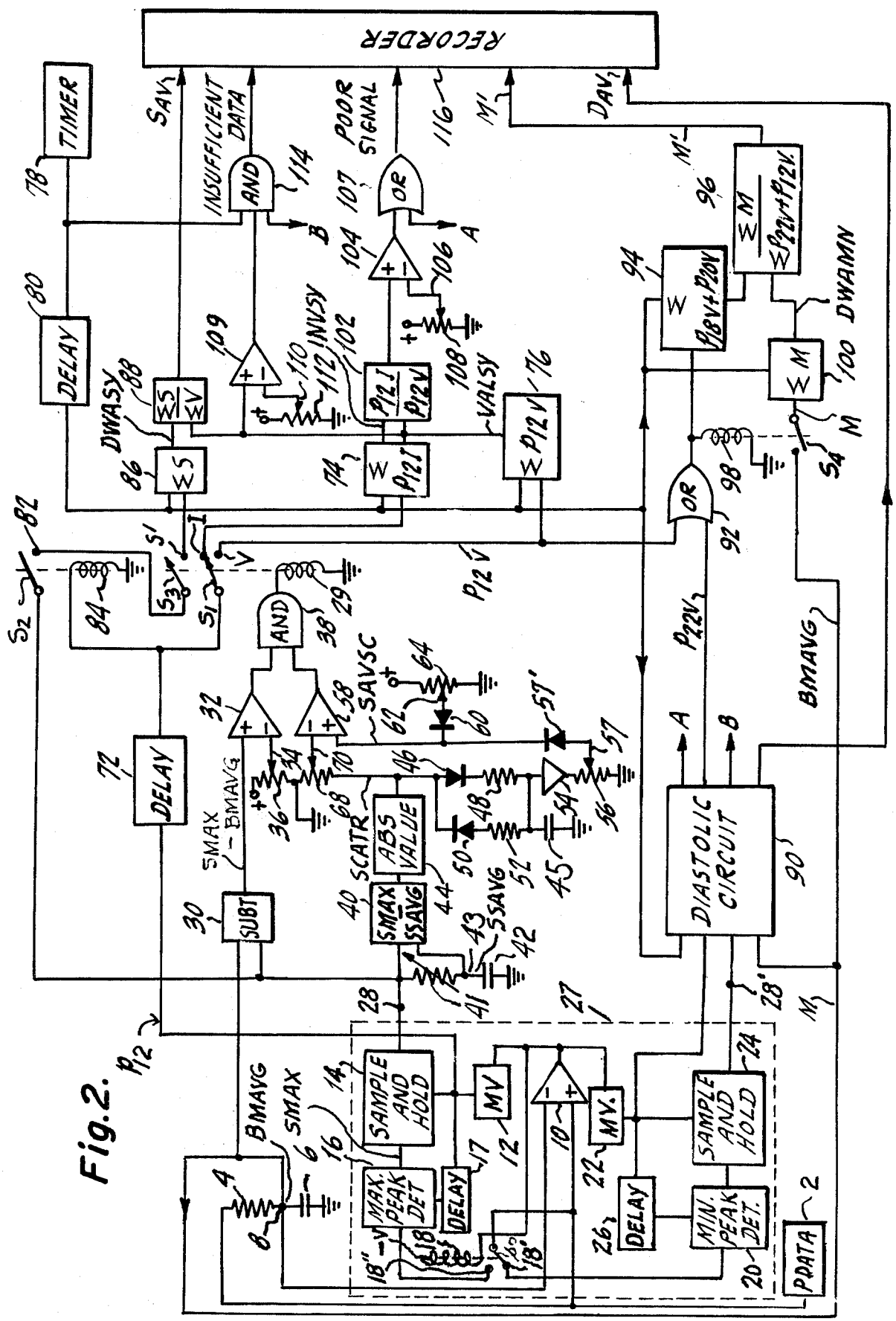
FIG. 2 is a schematic diagram of a circuit embodying the principles of this invention.

In the circuit of FIG. 2, the signal SMAX varies with the amplitudes of all peaks that are above the mean BMAVG, but some of these peaks may be due to spurious perturbations. Some of them can be eliminated by adding and subtracting offsets to the mean BMAVG, as described in my U.S. Patent Application entitled "Beat-to-Beat Systolic and Diastolic Indicator" and filed concurrently herewith, or by other means.

Instead of applying a filtered reference signal SSAVG to the subtractor 40, it would be possible to use a reference signal such as that provided by a means described in my U.S. Patent Application entitled "Derivation of Steady Values of Blood Pressures" and filed concurrently herewith, or by other commercially available means. In the apparatus disclosed in the latter application, the value of SSAVG is changed in response to each peak by an amount depending on the difference between the amplitude of the peak and the average amplitudes of a few preceding peaks. The larger the difference, the smaller is the change.

The input signal that is processed in the circuit of FIG. 2 is a continuous signal SMAX that represents the amplitude of each maximum peak of a blood pressure signal PDATA until the next maximum peak is encountered. The time constant of the low pass filter 41, 42 is chosen so as to produce a reference signal such as the voltage SSAVG that follows the amplitude variations at a rate no faster than the amplitude of the systolic blood pressure is expected to vary. Therefore, the absolute difference, SCATR, between the instantaneous amplitude of SMAX and SSAVG that is derived by the subtractor 40 and the absolute value circuit 44 represents the instantaneous amplitude deviation of SMAX from its expected value. The voltage SAVSC represents the average of these deviations and is permitted to follow decreases in the deviation more rapidly than increases. The time constant of the filters that derive SSAVG and SAVSC may vary depending on whether the input signal PDATA represents blood pressure or some other variable, but if it represents blood pressure, a time constant of 15 sec has been found to work well for the filter 41, 42 and time constants of 30 sec and 60 sec have been found to work well for the filters 48, 45, and 52, 45, respectively.

It would be possible to use a constant value for the reference SSAVG that is set by observation of SMAX so as to lie within a range of amplitude variations corresponding to the variations in the actual systolic pressure. The potentiometer taps 70 and 57 can be set so that the output of the comparator 58 will be negative for any deviation, SCATR, that is considered to be too great with respect to the average of such deviations, SAVSC, for the value of SMAX to be considered valid.

When the output signal of the AND gate 38 is high, indicating a valid value of SMAX, the pulses $P_{12}$ are applied to the integrator 76 via the switch $s_1$ and the samples of SMAX, which occur at the same time as the pulses $P_{12}$, are applied to the integrator 86 via the switches $s_2$ and $s_3$. When the output signal of the AND gate 38 is low, indicating an invalid value of SMAX, the pulses $P_{12}$ are applied to the integrator 74. The resetting of the integrators at periodic intervals by pulses from the timer 78 causes the voltage at the output of the integrator 76 to be proportional to the number of valid pulses $P_{12}$ received during the intervals, the voltage at the output of the integrator 86 to be proportional to the sum of all valid samples of SMAX, and the voltage at the output of the integrator 74 to be proportional to the number of invalid pulses $P_{12}$ received during the interval. The number of valid and invalid pulses $P_{12}$ are generally proportional to the intervals during which respectively invalid and valid values of SMAX occur. The divider 88 yields the average $S_{AV}$ of all the valid systolic samples, i.e., each sample contributes the same to $S_{AV}$, and the divider 102 yields a voltage proportional to the ratio of the number of invalid pulses $P_{12I}$ to the number of valid pulses $P_{12V}$. Pulse counters could be used in place of the integrators 74 and 76.

This sampling technique causes the value of $S_{AV}$ to be an average of the valid samples of SMAX regardless of the times between them and the times depend on the crossing of BMAVG by PDATA. Therefore, if the times are consistent or if the effects of differences in the times are to be ignored, the switch $s_2$ could be kept closed and a constant voltage could be applied to $s_1$. The output voltage of the integrator 76 would be proportional to the time within a period set by the timer 78 during which SMAX is valid, the output voltage of the integrator 74 would be proportional to the time within the period during which SMAX is invalid, and the voltage at the output of the integrator 86 would be the integrated value of valid values of SMAX. The dividers would operate as before. If the integrator 86 operates to obtain an average value of the valid values of SMAX, it may be necessary to insert ahead of it a circuit for converting the voltage SMAX into a corresponding current.

As illustrated, the validity of a value of SMAX depends on its amplitude as well as its deviation from an average of prior deviations, but either criteria could be used alone.

DESCRIPTION OF A DIGITAL SIGNAL PROCESSOR

Direct processing of the blood pressure signal PDATA at the output of the source 2 of FIG. 2 so as to derive maximum and minimum peaks and to determine which are valid and which are invalid in accordance with this invention can be carried out by digital logic circuits as well as by the analog circuits of FIG. 2. Circuits operating in this manner are described in connection with the Hewlett-Packard 21MX series computer, but it will be apparent to those skilled in the art that other computers could be used. It is contemplated that the computer will be an integral part of the monitoring equipment of which this invention forms a part.

Figure 3:
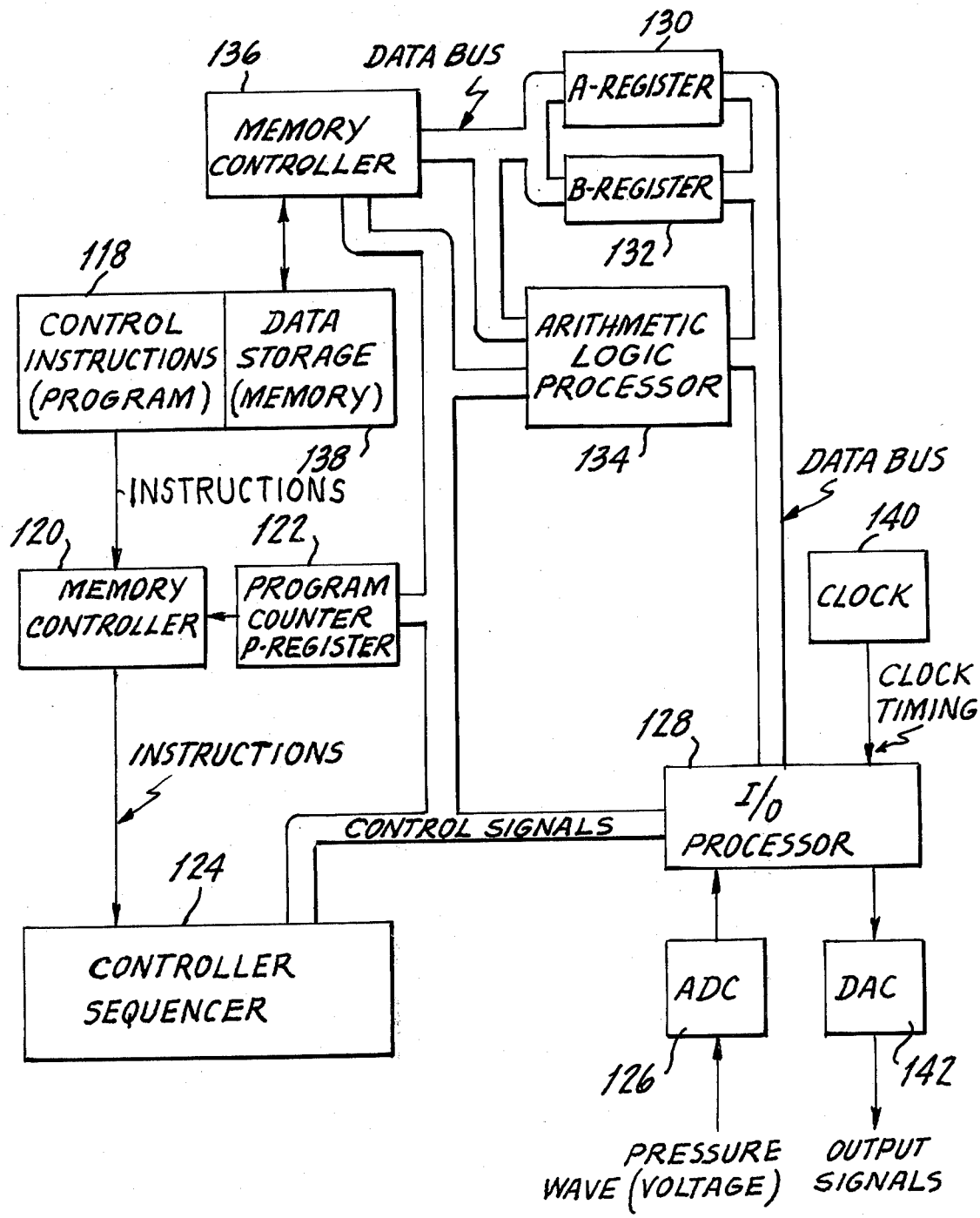
FIG. 3 is a block diagram of a computer for processing signals in accordance with this invention.

FIG. 3 is a block diagram of functional digital units required for carrying out the invention. Control of the flow of data as well as the operations performed on the data is determined by instructions stored at different locations in a ROM or instruction memory 118. Instructions are fetched from the memory 118 by a memory controller 120 in response to commands from a program counter or P register 122 and applied to a controller/sequence 124.

The analog blood pressure signal, PDATA, at the output of the source 2 of FIG. 2 is converted into its digital form by an analog-to-digital converter 126 and applied to an input of an input/output processor 128. The converter 126 samples the analog wave PDATA at intervals determined by a clock 140, which is separate and distinct from the computer clock, not shown, contained in the controller/sequencer 124. The sequencer controls the application of the digitized PDATA to an A register accumulator 130 and a B register accumulator 132 that are part of an arithmetic processor including an arithmetic logic processor 134, and it also may cause a memory controller 136 to take data from one of the accumulators 130 or 132 or the logic processor 134 and place it into a read/write RWM data storage memory 138 or vice-versa. The data storage memory 138 may share the same physical memory with the control instruction memory 118, and both memories may be controlled by the same memory controller, but separate memories and controllers are shown so as to more clearly identify the roles played by each.

All operations involving data manipulation generally take place in the accumulators 130 or 132. A program instruction may, for example, cause the controller/sequencer 124 to request the arithmetic logic processor 134 to perform some operation involving one or both of the accumulators. Whether the operation includes adding, dividing, negating, multiplying, shifting, rotating, Boolean manipulation (AND, OR), or testing, the results stay in an accumulator. If the value in the accumulator is to be stored in the data memory 138, a separate instruction will be given to the memory controller 136 by the controller/sequencer 124.

Instructions may be taken from the control instruction memory 118 by the memory controller 120 with a sequence other than normal by resetting the program counter 122 with the arithmetic logic processor 134 or with the controller/sequencer 124, e.g., a test compare instruction could result in the contents of the program counter or P register 122 being modified so as to cause it to select an alternate branch in the stream of program instructions derived from the control instruction memory 118.

An external clock 140 provides asynchronous timing pulses to the input/output processor 128 causing it to inform the controller/sequencer 124. This results in the program counter 122 being shifted to a timing section of the program that might, for example, request the input/output processor 128 to sample the analog blood pressure signal PDATA with the A-D converter 126 and place it in the data memory 138 via one of the accumulators 130 or 132. After the timing section of the program is completed, the program counter 122 is set back to allow the computer to resume its normal processing.

When all manipulations of data have been completed so as to derive a digital signal representative of a maximum or minimum peak of the blood pressure signal PDATA, the controller/sequencer 124 issues a command signal causing the input/output processor 128 to apply the digital signal to a digital-to-analog converter 142, that converts it to an analog signal corresponding to the systolic or diastolic peak in question.

Operation of the Digital Processor

The manner in which a Hewlett-Packard 21MX series computer processes signals representing the amplitudes of peaks of the signal PDATA so as to determine which are valid and to be included in the averages forming data points in the trend plot, and which are invalid and to be excluded therefrom will now be explained by reference to the flow charts of FIGS. 4A, 4B, 4C and 4D. A step in the program at the end of the specification that is pertinent to each block in the flow charts is set forth in nearby parentheses. Steps in the program indicated by an asterisk (*) are not actual computer steps, but are included for the purpose of explanation. Reference will be made where appropriate to circuit components of FIG. 2 and to the block diagram of the computer shown in FIG. 3, but identification of the figures referred to is not thought to be required in each case. It should be kept in mind that FIG. 2 only shows the details of the portion of the analog circuit that identifies the valid maximum values of the signal PDATA and processes them for display, whereas the program includes steps for processing both maximum and minimum values.

The digital form of an analog blood pressure signal such as PDATA of FIG. 1A that appears at the output of the source 2 of FIG. 2 is provided at the output of the analog-to-digital converter 126 of FIG. 3. It is transferred into the accumulator 130 as indicated in the block 144 of the portion of the flow chart shown in FIG. 4A. As only twelve significant bits are handled by the converter 126, the least significant four bits are set to zero because their values are not known. Negative blood pressures are not encountered so that if PDATA is negative, its value is arbitrarily set to zero. No equivalent function need be performed in the circuit.

If the equipment has just been turned on, this fact is indicated by a test in a learning decision block $D_1$ and the following initialization procedure is carried out. A learning flag is cleared in a block 146, a function not provided in the circuit. In the computer, the values of BMAVG, SSAVG, and SDAVG are set at the current value of PDATA, whereas in the circuit, the capacitors 6 and 44 and the capacitor, not shown, in the diastolic circuit 90 are respectively charged by the application of PDATA in the normal course of operation. A value SMAVG that is a more slowly varying version of BMAVG is also set to the value of PDATA, but there is no voltage corresponding to SMAVG in the circuit.

In order to identify in a manner to be explained the first sample of PDATA that is above a reference, such as BMAVG, the maximum peak detecting means is set at a unique value representing a pressure that is much lower than the detector will ever experience, and in order to identify the first sample of PDATA that is below the reference, the minimum peak detecting means is set at a unique value that is greater than the detector will ever experience. This function is performed in the circuit by the change in state at the output of the comparator 10.

Systolic Processing and Search for Minimum Value of DMIN

If $D_2$ indicates that PDATA is below BMAVG, a decision block $D_3$ in FIG. 4B tests whether this is the first sample below BMAVG. This is done by noting whether the value of DMIN is the unique value +32767, that is inserted in the data memory 138 during initialization by the block 148 or by a block 166' of FIG. 4C during normal operation. In the circuit, the identification of the first value of PDATA below BMAVG is done by the comparator 10. When $D_3$ indicates that a first sample of PDATA below BMAVG has been received, the following functions are performed.

Procedures set forth in a block 150 change the unique value of DMIN in the data storage memory 138 to PDATA. Succeeding samples of PDATA will therefore cause the block $D_3$ to give a negative answer rather than a positive answer. A negative answer activates a decision block $D_4$ and a block 152 that acts as a peak detecting means and searches for a minimum value of DMIN just as the detector 20 in the circuit. $D_4$ tests each sample of PDATA to determine if it represents a pressure less than the last value of DMIN. If it is not less, DMIN remains the same, but if it is less, the block 152 updates DMIN. In either case, proceed to point four in the flow charts or GMEAN in the program where a new value of BMAVG is calculated, as will be explained in connection with FIG. 4D.

An answer in $D_3$ indicating that a first sample of PDATA has been received that is below the threshold also causes the following functions to be performed. A block 154 derives the value of SCATR by subtracting the old value of SSAVG, the derivation of which will be explained, from the current value of SMAX. The value of SMAX is provided by the circuits of the rectangle 27 of FIG. 2 or other apparatus, and the absolute value of the systolic SCATR is derived by the subtractor 40 and the absolute value circuit 42. The value of SSAVG to be used in the next subtraction is determined as indicated in block 156 wherein the difference between the current value of SMAX and the old value of SSAVG is divided by some constant such as 16 and the result added to the old value of SSAVG. This function is performed in the circuit by the filter comprised of the resistor 41 and the capacitor 42.

The block 158 indicates the calculation of the value of SMAVG, a value not indicated in the circuit but which would be used at the terminal of switch s4 in place of BMAVG. It is derived by subtracting the old value of SMAVG from the new value of BMAVG, dividing by a constant such as 32 and adding the result to the old value of SMAVG. Thus, in effect, SMAVG is a slowly changing average of BMAVG.

The value of SAVSC that is provided in the circuit at the tap 57 is calculated as indicated in the block 160 by subtracting the old value of SAVSC from the new value of SCATR, dividing by a constant such as 32 when SCATR-SAVSC is decreasing and by a larger constant such as 64 when SCATR-SAVSC is increasing and adding the result to the old value of SAVSC. The next time around, the new value of SAVSC just calculated becomes the old value. Division by the different constants 32 and 64 corresponds to the different time constants provided by the RC filter 52, 44 or 48, 44 depending on the polarity of the signal change. The minimum value noted in the block 160 is determined in the circuit by the potentiometer 64 acting through the diode 60.

As will be recalled from the discussion of the circuit of FIG. 2, a value SMAX had to meet two criteria in order to be considered valid. The first is that the value of SCATR must not exceed SAVSC by more than a predetermined amount, and the second is that the value of SMAX has to exceed BMAVG by a predetermined amount. Whether these criteria were met was determined by the comparators 58 and 32, and the meeting of both criteria resulted in the energization of the relay coil 29. In the computer, the first criteria is determined in the decision block $D_5$ and the second in decision block $D_6$. If the tests in either block indicates that its criteria is not met, a block 162 increments the number of invalid values of SMAX in a counter that corresponds to the integrator 74.

On the other hand, if the blocks $D_5$ and $D_6$ both indicate that their respective criteria are met, a fact that results in the energization of the relay coil 29 in the circuit, the functions indicated in the block 164 are performed. The number of valid systolic values of SMAX is maintained corresponding to the voltage VALSY at the output of the integrator 76. The summation of the valid values of SMAX are accumulated corresponding to the output DWASY of the integrator 86, and the summation of mean average DWAMN is updated by adding the new value of SMAVG to the old value of DWAMN. In the circuit, the value of DWAMN is slightly different because the values of BMAVG (SMAVG is not in the circuit) occurring when valid pulses $P_{12V}$ or $P_{22V}$ are applied to the OR gate 92 are integrated in the integrator 100. The divisions performed by the dividers 88, 102 and 96 so as to respectively attain a value of $S_{AV}$, the ratio of invalid to valid values of SMAX, and the value of M' are not shown because they would operate as part of a separate functional module, but could easily be programmed by one skilled in the art. After all these functions are performed, the value of SMAX is set to −32768 in the block 166 so as to allow the decision block $D_3$ of FIG. 4C to identify the first sample of PDATA that is above the threshold.

Distolic Processing and Search for a Maximum Value of SMAX

Figure 4A:
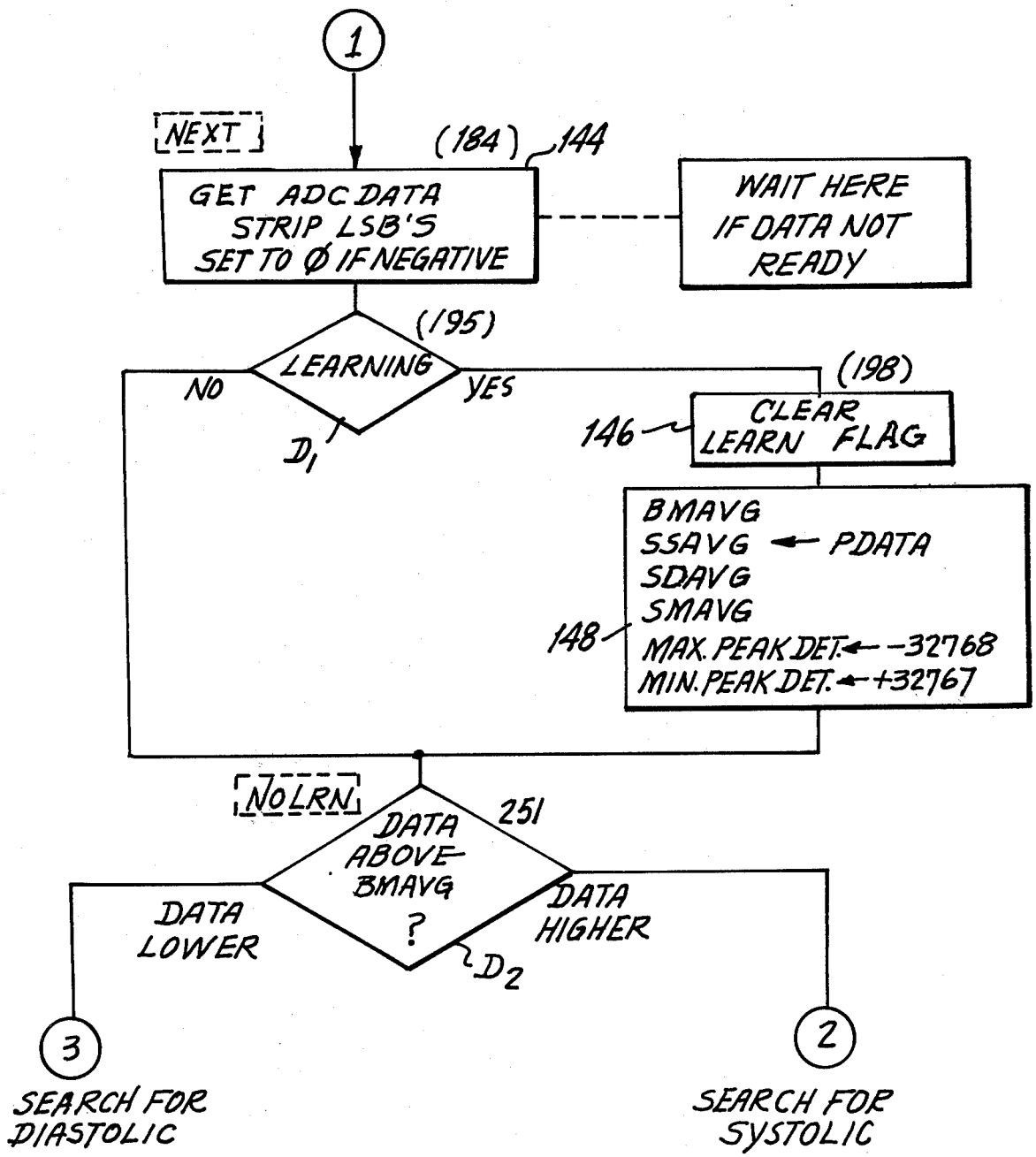
FIGS. 4A, 4B, 4C and 4D are flow charts illustrating a way of carrying out the invention with the aid of a computer in accordance with a program set forth in the specification.
Figure 4B:
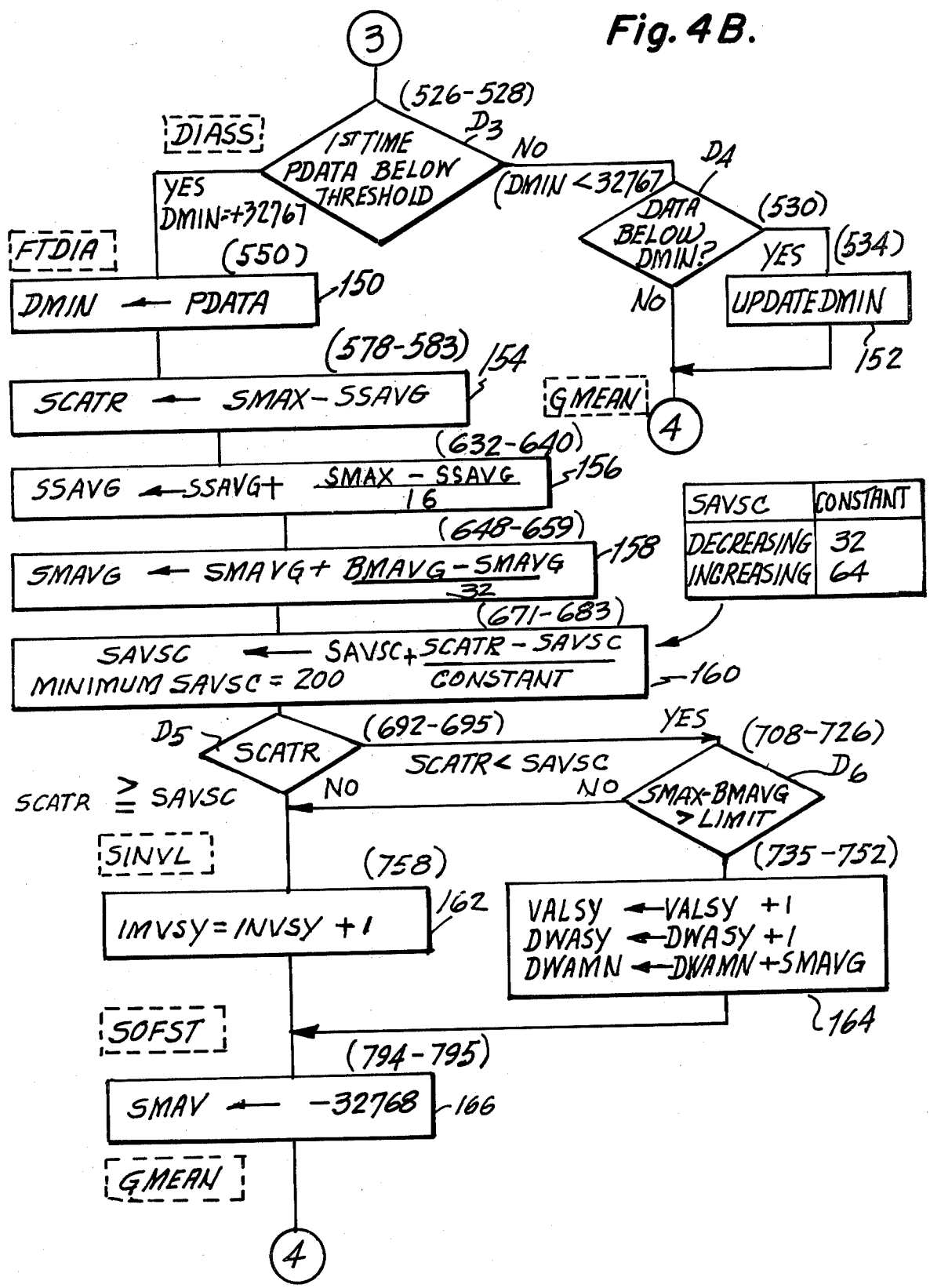
Figures 4C, 4D:
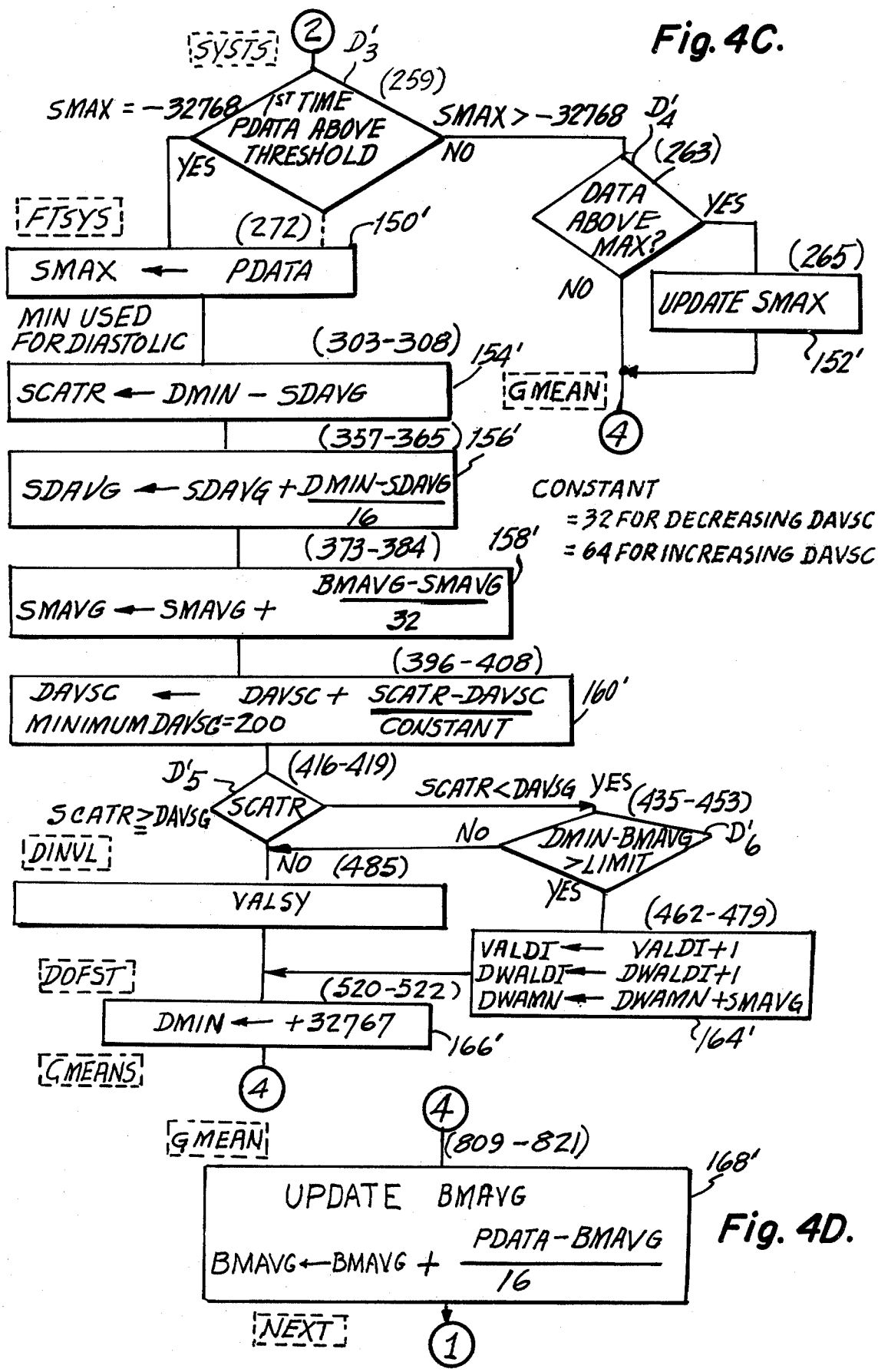

If the decision block $D_2$ of FIG. 4A indicates that PDATA is above BMAVG, the functions indicated in the portion of the flow chart in FIG. 4C are performed. Because they are similar to the functions just described in connection with FIG. 4B, components for similar functions are indicated by the same designations primed.

Determination of whether or not a sample of PDATA is the first sample above threshold is performed in the decision block $D_3'$ by noting whether the value of SMAX stored in the data memory 138 has the unique value of −32768 which it was set to in the block 166 of FIG. 4B. If SMAX has this unique value, all the functions of the blocks 150' and 154' through 166' are carried out. Because the block 150' sets the value of SMAX to PDATA in response to the first sample of PDATA above BMAVG and then to the value of the amplitude of that sample, SMAX no longer has the unique value, so that subsequent pulses cause $D_3'$ to yield a negative answer and cause the minimum peak detecting means comprised of $D_4'$ and 152' to search for a new minimum value of DMIN.

Calculation of BMAVG

During the time that the minimum peak detecting means $D_4$, 152 of FIG. 4B is searching for a minimum value of DMIN and subsequently during the time the maximum peak detecting means $D_4'$, 152' of FIG. 4C is searching for a maximum value of SMAX, the value of BMAVG is updated by every new sample of PDATA as indicated in block 168 of FIG. 4D. The difference between the current sample of PDATA and the former value of BMAVG is divided by a constant such as 16 and added to the former value of BMAVG. This function is performed in the circuit of FIG. 2 by the low pass filter comprised of the resistor 4 and the capacitor 6.

Example Calculation

That the hardware of the computer is controlled in a manner that is fully equivalent to the operation of the hardware represented in the schematic diagram of FIG. 2 will now be illustrated by an example. Reference will be made to the block diagram of the computer illustrated in FIG. 3 when appropriate.

Let us consider the resistor 4 and capacitor 6 that filter the input value PDATA to derive its approximate mean BMAVG. The equivalent function is performed by the computer program steps 809 through 819 that occur at the label GMEAN in the program and on the flow chart. The mathematical basis of this computation is described in lines 800 to 807 of the program. It may be shown that if this computation is performed at a regular interval, with a value of PDATA representing the input to the RC filter 4, 6 that the value BMAVG derived by the computer will behave identically as a function of time to the voltage BMAVG on the capacitor 6.

This computation is implemented in the computer as follows. The instruction on line 809 causes the memory controller 136 to retrieve the numeric value representing BMAVG from the data storage memory 138 and enter this value into the A register 130. The next instruction on line 810 causes the contents of the A register 130 to be negated. The instruction on line 811 causes the value PDATA to be retrieved from the data memory 138 and added to the contents of the A register 130, the result, PDATA-BMAVG, remaining in that register. The instructions on lines 812 and 813 cause the contents of the A register 130 to be shifted to the right four places. This results in the binary value, PDATA-BMAVG, being divided by 16. This operation is performed by the arithmetic and logic processor 134 of the computer and the results remain in the A register 130. The next two instructions are provided to prevent deadband when the divisor has a value lying between 0 and 15, and is therefore not represented in the RC equivalent. In line 818, the instruction causes the value BMAVG to be fetched from memory 138 by the memory controller 136 and added to the A register accumulator. The last instruction causes the contents of the A register to be stored back into memory 138, replacing and updating the original value of BMAVG.

This process takes place for each new sample of PDATA which is acquired by the analog-to-digital converter at an arbitrary rate. A rate of 50 samples per second has been found to be suitable.

Program To Be Used with a Hewlett-Packard 21MX Series Computer

```
0157   *
0158   *      GET NEXT DATA POINT FROM PRESSURE BUFFER
0159   *
0160   *
0161   NEXT  LDX  PPRCW
0162   *
0173         LDA  B,I       GET DATA
0180   *
0181         AND  =B177760  STRIP 4 LSB'S
0182         SSA
0183         CLA            DON'T ALLOW NEGATIVE
0184         STA  PDATA
0185   *
0186   *
0187   *      CHECK FOR LEARNING BIT SET
```

```
0188    *           IF SET USE CURRENT DATA FOR STATUS DISPLAY
0189    *           STARTING VALUES.
0190    *
0191    *
0192         LDA LEARN
0193         CLF 0
0194         AND PCTPT,I    PCW
0195         SZA,RSS
0196         JMP NOLRN
0197    *
0198         CMA
0199         AND PCTPT,I    CLEAR LEARNING BIT
0200         STA PCTPT,I
0201         STF 0
0202    *
0203         LDA PDATA
0204         STA SDAVG
0205         STA SMAVG
0206         STA SSAVG
0207    *
0232         ISZ INVDI      BUMP INVALID DIASTOLIC COUNT
0233         ISZ INVSY      BUMP INVALID SYSTOLIC COUNT
0234    *
0235         LDA MIN#
0236         STA SMAX       SET TO ENSURE
0237         LDA MAX#       THAT A BEAT
0238         STA DMIN          WILL BE FOUND NEXT TIME
0239    *
0240         LDA PDATA      CURRENT VALUE
0241         STA BMAVG      SET STATUS VALUES
0242         STA FDAVG
0243         STA FSAVG
0244    *
0245    *
0246         SKP
0247    *                   SYSTOLIC OR DIASTOLIC SEARCH?
0248    NOLRN CLB
0249    S/D? LDA PDATA
0250         ADB BMAVG
0251         JSB CMPAB         A CONTAINS PDATA
0252         JMP SYSTS      ABOVE THRESHOLD
0253         JMP DIASS      BELOW TH    A<B
0254    *                        TH IS BMAVG
0255         HED               SEARCH FOR NEXT SYSTOLIC VALUE
0256         SPC 2
0257    *                   NEW DATA VALUE IS IN "A" REG (PDATA)
0258    *
0259    SYSTS LDB SMAX     PREVIOUS MAX
0260         CPB MIN#
0261         JMP FTSYS      FIRST TIME IN!
0262    *
0263         JSB CMPAB          NEW MAX ?
0264    *
0265         STA SMAX       NEW MAX
0266         JMP GMEAN
0267         HED                 PROCESSING OF NEW DIASTOLIC VALUES
0268    *    FIRST TIME ON SYSTOLIC SIDE OF FENCE
0269    *    CALL THIS THE START OF A NEW BEAT
0270    *
0271    *
0272    FTSYS EQU *         FIRST TIME SYSTOLIC
0273    *
0274    *    SET SYSTOLIC TO CURRENT VALUE
0275         STA SMAX
0276    *
0300    *
0301    *    COMPUTE SCATTER FROM SLOW AVERAGE:
0302    *
0303         LDB SDAVG      SLOW DIAST AVG
0304         CMB,INB
0305         ADB DMIN       DIAST - SLOW AVG
0306         SSB
0307         CMB,INB        TAKE ABSOLUTE VALUE
0308         STB SCATR
0309    *
0335    *    UPDATE SLOW AVERAGE
0336    *
0337    *
0338    *
0339    *
0340    *
0341    *
0342    *
0343    *    THIS ROUTINE UPDATES A RUNNING AVERAGE BY THE METHOD
0344    *
```

```
0345  *    RAVG = (1.0 - FACTOR) * RAVG + FACTOR * NEWVAL
0346  *
0347  *    (RAVG = RAVG + FACTOR *(NEWVAL - RAVG)
0348  *
0349  * THIS HAS AN EXPONENTIAL TIME RESPONSE SIMILAR TO AN R-C FILTER
0350  *
0351  *
0352  *    USE FACTOR = 1/SMOTH,
0353  *
0354  *
0355  *                SMOTH=10 GIVES 98% STEP RESPONSE IN 62 BEATS
0356  *
0357        LDA SDAVG
0358        CMA,INA
0359        ADA DMIN        DIAST-SLOW AVG
0360        CLB
0361        SSA
0362        CCB             EXTEND NEG SIGN
0363        DIV SMOTH       DIAST=AVG/SMOTH
0364        ADA SDAVG       TRUNCATED, NOT ROUNDED
0365        STA SDAVG
0366  *
0367  *
0368  *
0369  *SIMILARLY, UPDATE MEAN SLOW AVERAGE
0370  *
0371  *
0372  *
0373        LDA SMAVG
0374        CMA,INA
0375        ADA BMAVG       MEAN RUNNING AVG - MEAN SLOW AVG
0376        CLB
0377        SSA
0378        CCB             EXTEND NEG SIGN
0379        DIV SMOTH       NEW = AVG/SMOTH
0380  *
0381        ARS             DIV BY 2
0382  *
0383        ADA SMAVG       TRUNCATED, NOT ROUNDED
0384        STA SMAVG
0385  *
0386  *
0387        SPC 2
0388  *
0389  *   UPDATE SCATTER AVERAGE
0390  *
0391  *   SIMILAR AVERAGE
0392  *      FACTOR IS 1/32
0393  *           GIVING TIME CONSTANT OF 42 BEATS
0394  *
0395  *
0396        LDB DAVSC       DIAST AVG SCATTER
0397        CMB,INB
0398        ADB SCATR
0399        ASR 5           DIVIDES BY 32  ("A" IS LOST)
0400        SSB,RSS         IF AVG IS INCREASING
0401        BRS               SLOW RATE
0402        ADB DAVSC
0403  *
0404        LDA =D200
0405        JSB CMPAB
0406        LDB =D200       SET MINIMUM VALUE
0407  *
0408        STB DAVSC
0409  *
0411  *   CHECK FOR VALID/INVALID DIAST VALUE FOR THIS BEAT
0412  *      INVALID IS DEFINED TO HAVE A SCATTER VALUE
0413  *          GREATER THAN THE AVERAGE SCATTER
0414  *
0415  *
0416        LDA SCATR       "B" HAS AVG VALUE
0417        INB             ALLOW A=B VALID
0418        JSB CMPAB
0419        JMP DINVL       INVALID VALUE   A<B
0420  *
0421  *
0422        SPC 2
0423  *
0424  *
0425  *          CHECK FOR PULSE PRESSURE
0426  *      CALL BEAT INVALID IF PULSE IS NOT FOUND
0427  *
0428  *
0429  *
```

```
0430  *     LIMIT VALUES FROM TABLE IN PRGSV:
0431  *
0432  *              NO PULSE IF LESS THAN TABLE VALUE FROM MEAN
0433  *
0434  *
0435        LDA USRNO
0436        MPY NPCH        GET POINTER
0437        ADA PRCTA'      TO THIS USER'S ENTRIES
0438        CMA,INA         IN THE PRES CONTROL TABLE.
0439  *
0440        ADA PCTPT       # OFFSET IN TABLE
0441  *
0442        ADA PPRAD       PULSE PRESSURE TABLE ADDRESS
0443  *
0444        LDB A,I         GET MINIMUM PULSE PRESSURE IN ADC UNITS
0445  *
0446        LDA DMIN        DIASTOLIC
0447        CMA,INA
0448        ADA BMAVG       MEAN-DIAST
0449  *
0450        JSB CMPAB            SKIP IF DIFFERENCE TOO SMALL
0451  *
0452        RSS             OK
0453        JMP DINVL       INVALID !!!
0454  *
0455  *
0456        SPC 2
0457  *
0458  *
0459  *     VALID!!!!!
0460  *
0461  *
0462        ISZ VALDI       DIAST VALID COUNT
0463        LDA DMIN        DIAST VALUE
0464        CLE
0465        ADA DWADI       LSB'S DOUBLE WORD ACCUMULATOR
0466        STA DWADI
0467        SEZ             CHECK OVERFLOW
0468        ISZ DWADI+1     BUMP MSB'S
0469  *
0470  **  SAME THING FOR CURRENT MEAN VALUE
0471  *
0472        LDA SMAVG       SLOW MEAN AVG
0473        CLE
0474        ADA DWAMN
0475        STA DWAMN
0476        SEZ
0477        ISZ DWAMN+1
0478  *
0479        JMP DOFST
0480  *
0481        SPC 2
0482  *
0483  *     INVALID !!!!
0484  *
0485  DINVL ISZ INVDI       INVALID DIAST COUNTER
0486  *
0517  *
0518  *     SET MIN FOR NEXT TIME
0519  *
0520  DOFST LDA MAX#
0521        STA DMIN
0522        JMP GMEAN
0523        HED                  NEXT DIASTOLIC VALUE SEARCH
0524  *
0525  *
0526  DIASS LDB DMIN
0527        CPB MAX#        FIRST TIME?
0528        JMP FTDIA       YES!
0529  *
0530        JSB CMPAB            NEW MIN?
0531  *
0532        JMP GMEAN       NO
0533  *
0534        STA DMIN        YES
0535        JMP GMEAN
0536  *
0537  *
0538        HED                  PROCESSING OF NEW SYSTOLIC VALUES
0539  *     FIRST TIME INTO DIASTOLIC REGION
0540  *          TAKE PREVIOUS MAX AS SYSTOLIC FOR THIS BEAT
0541  *          RESET OFFSET
0542  *          RESET FOR NEXT TIME
0543  *
0544  *
```

```
0545  *
0546  *
0547  FTDIA EQU *           FIRST TIME DIASTOLIC
0548  *
0549  *   SET DIASTOLIC TO CURRENT VALUE
0550      STA DMIN
0551  *
0575  *
0576  *   COMPUTE SCATTER FROM SLOW AVERAGE:
0577  *
0578      LDB SSAVG       SLOW SYST AVG
0579      CMB,INB
0580      ADB SMAX        SYST - SLOW AVG
0581      SSB
0582      CMB,INB         TAKE ABSOLUTE VALUE
0583      STB SCATR
0584  *
0585      SPC 2
0586  *
0609  *
0610  *   UPDATE SLOW AVERAGE
0611  *
0617  *
0618  *   THIS ROUTINE UPDATES A RUNNING AVERAGE BY THE METHOD
0619  *
0620  *   RAVG = (1.0 - FACTOR) * RAVG + FACTOR * NEWVAL
0621  *
0622  *   (RAVG = RAVG + FACTOR *(NEWVAL - RAVG)
0623  *
0624  *   THIS HAS AN EXPONENTIAL TIME RESPONSE SIMILAR TO AN R-C FILTER
0625  *
0626  *
0627  *       USE FACTOR = 1/SMOTH,
0628  *
0629  *
0630  *               SMOTH=16 GIVES 98% STEP RESPONSE IN 62 BEATS
0631  *
0632      LDA SSAVG
0633      CMA,INA
0634      ADA SMAX        SYST-SLOW AVG
0635      CLB
0636      SSA
0637      CCB             EXTEND NEG SIGN
0638      DIV SMOTH       SYST-AVG/SMOTH
0639      ADA SSAVG       TRUNCATED, NOT ROUNDED
0640      STA SSAVG
0643  *
0644  *SIMILARLY, UPDATE MEAN SLOW AVERAGE
0645  *
0646  *
0647  *
0648      LDA SMAVG
0649      CMA,INA
0650      ADA BMAVG       MEAN RUNNING AVG - MEAN SLOW AVG
0651      CLB
0652      SSA
0653      CCB             EXTEND NEG SIGN
0654      DIV SMOTH       NEW - AVG/SMOTH
0655  *
0656      ARS             DIV BY 2 TO SLOW AVG
0657  *
0658      ADA SMAVG       TRUNCATED, NOT ROUNDED
0659      STA SMAVG
0660  *
0663  *
0664  *   UPDATE SCATTER AVERAGE
0665  *
0666  *   SIMILAR AVERAGE
0667  *       FACTOR IS 1/32
0668  *           GIVING TIME CONSTANT OF 42 BEATS
0669  *
0670  *
0671      LDB SAVSC       SYST AVG SCATTER
0672      CMB,INB
0673      ADB SCATR
0674      ASR 5           DIVIDES BY 32 ("A" IS LOST)
0675      SSB,RSS         IF AVG IS INCREASING
0676      BRS             SLOW RATE
0677      ADB SAVSC
0678  *
0679      LDA =D200
0680      JSB CMPAB
0681      LDB =D200       SET MINIMUM VALUE
0682  *
0683      STB SAVSC
0684  *
```

```
0685        SPC 2
0686   *
0687   *    CHECK FOR VALID/INVALID SYST VALUE FOR THIS BEAT
0688   *       INVALID IS DEFINED TO HAVE A SCATTER VALUE
0689   *           GREATER THAN THE AVERAGE SCATTER
0690   *
0691   *
0692        LDA SCATR      "B" HAS AVG VALUE
0693        INB            ALLOW EQUAL TO BE VALID
0694        JSB CMPAB
0695        JMP SINVL      INVALID VALUE
0696   *
0697        SPC 2
0698   *            CHECK FOR PULSE PRESSURE
0699   *       CALL BEAT INVALID IF PULSE IS NOT FOUND
0700   *
0701   *
0702   *
0703   *    LIMIT VALUES FROM TABLE IN PRGSV:
0704   *
0705   *            NO PULSE IF LESS THAN TABLE VALUE FROM MEAN
2726   *
2727   *
2728        LDA USRNO
0709        MPY NPCH       GET POINTER
0710        ADA PRCTA      TO THIS USER'S ENTRIES
0711        CMA,INA         IN THE PRES CONTROL TABLE.
0712   *
0713        ADA PCTPT      @ OFFSET IN TABLE
0714   *
0715        ADA PPRAD      PULSE PRESSURE TABLE ADDRESS
0716   *
0717        LDB A,I        GET MINIMUM PULSE PRESSURE IN ADC UNITS
0718   *
0719        LDA BMAVG      MEAN
0720        CMA,INA
0721        ADA SMAX       SYSTOLIC-MEAN
0722   *
0723        JSB CMPAB          SKIP IF DIFFERENCE UNDER LIMIT
0724   *
0725        RSS            OK
0726        JMP SINVL      INVALID !!!
0731   *
0732   *    VALID!!!!!!
0733   *
0734   *
0735        ISZ VALSY      SYST VALID COUNT
0736        LDA SMAX       SYST VALUE
0737        CLE
0738        ADA DWASY      LSB'S DOUBLE WORD ACCUMULATOR
0739        STA DWASY
0740        SEZ            CHECK OVERFLOW
0741        ISZ DWASY+1    BUMP MSB'S
0742   *
0743   **   SAME THING FOR CURRENT MEAN VALUE
0744   *
0745        LDA SMAVG      SLOW MEAN AVG
0746        CLE
0747        ADA DWAMN
0748        STA DWAMN
0749        SEZ
0750        ISZ DWAMN+1
0751   *
0752        JMP SOFST
0753   *
0755   *
0756   *    INVALID !!!!
0757   *
0758   SINVL ISZ INVSY     INVALID SYST COUNTER
0759   *
0760   *
0791   *
0792   *    SET MAX FOR NEXT TIME
0793   *
0794   SOFST LDA MINB
0795        STA SMAX
0796   *
0797   *
0798   *
0799        HED  << PPROC >>   BEAT TO BEAT MEAN CALCULATION
0800   *    THIS ROUTINE UPDATES A RUNNING AVERAGE BY THE METHOD
0801   *
0802   *    RAVG = (1.0 - FACTOR) * RAVG  +  FACTOR * NEWVAL
0803   *
0804   *    (RAVG = RAVG + FACTOR *(NEWVAL - RAVG)
0805   *
```

```
0806   *      USE FACTOR = 1/16    GIVES TIME CONSTANT OF 20 SAMPLES
0807   *               20 * 20 MSEC  =  0.4 SEC
0808   *
0809   GMEAN  LDA BMAVG       OLD AVG
0810          CMA,INA
0811          ADA PDATA       NEW VALUE
0812          ARS,ARS
0813          ARS,ARS         DIVIDE BY 16
0814   *
0815          SSA,RSS         DITHER FOR VALUES BETWEEN 0 AND 15
0816          INA
0817   *
0818          ADA BMAVG
0819          STA BMAVG
0820   *
0821          JMP NEXT        NEXT DATA VALUE
0822          SPC 4
0823   *
0824   *
0825   MIN#   DEC =32768
0826   MAX#   DEC 32767
0827   TMOUT  DEC =250        SET FOR 5 SECONDS AT 50 HZ
0828   *
0829   *
0830   *
0831   *
0832   *
0833          HED CMPAB ROUTINE
0834   *
0835   *
0836   *
0837   *
0838   *      THIS ROUTINE RETURNS TO P+1 IF A = OR > B
0839   *      THIS ROUTINE RETURNS TO P+2 IF A < B
0840   *
0841   CMPAB  NOP
0842          CMB,INB         NOTE!
0843          ADB A           E AND O REGISTERS LOST!
0844          CMB,SSB,INB,RSS
0845          ISZ CMPAB
0846          ADB A
0847          JMP CMPAB,I
0848   *
0849          END
```

What is claimed is:

1. Apparatus for processing samples of an input signal that represents values of phenomena of which measurement is desired and which lie in within an expected range and which may include noise which may extend outside said range, comprising
    means for producing a reference value representing an value that approximates the center of said range,
    means for deriving difference signals representing the absolute difference between the value of each of said samples and the value of said reference signal,
    means for deriving a signal representing a running average of at least some of said difference signals, and
    means for producing an output signal having a first value indicating that the sample represents noise when the magnitude of a difference signal exceeds a predetermined relationship to the said running average of said difference signals and a second value indicating that the sample represents the desired measurement when the magnitude of said difference signal is less than the predetermined relationship to the average of said difference signals.

2. Apparatus as set forth in claim 1 wherein means are provided for counting within a given time period the number of samples occurring while said output signal has said first value.

3. Apparatus as set forth in claim 1 wherein means are provided for counting within a given time period the number of samples occurring while said output signal has said second value.

4. Apparatus as set forth in claim 3 wherein means are provided for indicating that the input signal has insufficient data when the number of samples is less than a predetermined number.

5. Apparatus as set forth in claim 1 wherein means are provided for counting within a given time period the number of samples occurring while said output signal has said first value and the number of samples occurring while said output signal has said second value.

6. Apparatus as set forth in claim 5 wherein means are provided for producing a signal indicative of the ratio of the number of samples occurring when the output signal has said first value to the number of samples occurring when the output signal has said second value.

7. Apparatus as set forth in claim 6 wherein means are provided for indicating that the input signal has a poor quality when said ratio exceeds a predetermined value.

8. Apparatus as set forth in claim 1 wherein said reference signal is derived from previous samples of said input signal.

9. Apparatus as set forth in claim 1 wherein the means for providing the signal representing the running average of said difference signals operates to change said average more when the difference between said difference signal and the said average signal is of one sign than when it is of the other.

10. Apparatus as set forth in claim 1 wherein the samples represent the values of the systolic peaks of blood pressure.

11. Apparatus as set forth in claim 1 wherein the samples represent the values of the diastolic peaks of blood pressure.

12. Apparatus as set forth in claim 1 wherein means are provided for producing an average of the values of said input signal when said output signal has one of said first and second values.

13. Apparatus as set forth in claim 1 wherein said means for providing the reference signal derives an average of the input signal.

14. Apparatus for processing an input signal including a desired component that varies slowly in value within an expected range but which may include undesired, spurious, sudden changes in amplitude extending outside said range, comprising means for providing a reference signal representing an average value of the input signal, means for deriving a difference signal representing the difference in amplitude between said input signal and said reference signal, means for deriving an average difference signal representing an average of the differences represented by said difference signal, and means for producing a first output signal when the value represented by said difference signal exceeds a given relationship to said average of the difference signals, and for producing a second output signal when the said difference signal is less than the given relationship to an average of the difference signals.

15. Apparatus as set forth in claim 14 wherein means are provided for deriving a signal representing the average of at least some of the values of said input signal occurring within a predetermined interval during the presence of said first output signal.

16. Apparatus as set forth in claim 14 wherein means are provided for producing said first output signal when said difference signal is smaller than a predetermined value.

17. Apparatus as set forth in claim 14 wherein the said means for deriving an average difference signal changes the average difference signal by a greater amount in response to a decrease in the value represented by the difference signal than it does to an increase in the value.

18. A method of processing a signal representing the variation of blood pressure with time in such manner as to provide a value representing the average of one of the systolic and diastolic blood pressures in which the effects of noise are substantially reduced, comprising deriving from the signal representing blood pressure sample values representing one of said systolic and diastolic blood pressures for each heartbeat, determining the absolute value of the absolute deviation of each sample value from an average of said sample values, deriving an average of said absolute deviations, and deriving an average of those sample values having a deviation that is less than a predetermined portion of the average of said absolute deviations.

19. Apparatus for deriving from a signal that represents the variation of blood pressure with time values representing one of the systolic and diastolic blood pressures that are relatively free from the effects of noise, comprising means for deriving from a blood pressure signal desired peak values representing one of the systolic and diastolic blood pressure values for each heartbeat, which desired peak values may include undesired peaks of noise having amplitudes that may extend outside of the expected amplitude range of the desired peak value, means for deriving from the output of said means a reference value representing a long-term average of the desired and undesired peak values, means for deriving the value of the absolute difference between each peak value and said reference value, means for deriving an average of the values of absolute difference, means for producing a first output value when the value of the absolute difference of a peak value and said reference value exceeds a predetermined portion of said average of the values of absolute difference, means for producing a second output value when the value of the absolute difference of a peak value and said reference value is less than said predetermined portion of said average of the values of absolute difference, and means for deriving an average of the desired peak values that produce said second output value during a predetermined interval of time.

* * * * *